United States Patent [19]

Zengel et al.

[11] 4,259,258

[45] Mar. 31, 1981

[54] PREPARATION OF BIS-N-CHLORAMIDES OF CYCLOALIPHATIC CARBOXYLIC ACIDS

[75] Inventors: Hans-Georg Zengel, Kleinwallstadt; Manfred Bergfeld, Erlenbach am Main, both of Fed. Rep. of Germany

[73] Assignee: Akzona Incorporated, Asheville, N.C.

[21] Appl. No.: 928,118

[22] Filed: Jul. 26, 1978

Related U.S. Application Data

[63] Continuation of Ser. No. 651,084, Jan. 21, 1976, abandoned.

[30] Foreign Application Priority Data

Jan. 22, 1975 [DE] Fed. Rep. of Germany ....... 2502412

[51] Int. Cl.$^3$ .......................................... C07C 103/737
[52] U.S. Cl. ............................................... 260/543 A
[58] Field of Search ............ 260/543 A, 557 R, 558 R

[56] References Cited

U.S. PATENT DOCUMENTS

| | | | |
|---|---|---|---|
| 3,657,324 | 4/1972 | Sheppard et al. | 260/543 A |
| 3,746,760 | 7/1973 | Sheppard et al. | 260/543 A |
| 3,914,267 | 10/1975 | Rennie et al. | 260/543 A |
| 3,917,688 | 11/1975 | Barton et al. | 260/543 A |

FOREIGN PATENT DOCUMENTS

| | | | |
|---|---|---|---|
| 812357 | 3/1974 | Belgium. | |
| 909455 | 9/1957 | Fed. Rep. of Germany | 260/543 A |
| 7402871 | 9/1974 | Netherlands. | |
| 7402872 | 9/1974 | Netherlands. | |

OTHER PUBLICATIONS

Zengel et al., Chem. Abstr. 82:43067(n) (1975) Abst. German Off. No. 2,313,548 (10/3/74), and U.S. Pat. No. 3,965,172.

Zengel et al., Chem. Abstr. 82:43043(u) (1975) Abstr. German Off. No. 2,313,496 (10/3/74), and U.S. Pat. No. 3,897,498.

*Primary Examiner*—Jane S. Myers
*Attorney, Agent, or Firm*—Francis W. Young; Robert F. Green

[57] ABSTRACT

Novel Bis-N-chloramides of aromatic dicarboxylic acids, such as alkyl-isophthalic or alkyl terephthalic acid, or of cycloaliphatic dicarboxylic acids such as cyclohexane dicarboxylic acid, are obtained by chlorinating the corresponding diamides, in an aqueous acid medium at a temperature of about 0° to 40° C.

3 Claims, No Drawings

PREPARATION OF BIS-N-CHLORAMIDES OF CYCLOALIPHATIC CARBOXYLIC ACIDS

This is a continuation of application Ser. No. 651,084, filed Jan. 21, 1976, now abandoned.

BACKGROUND OF THE INVENTION

This invention relates to novel bis-N-chloramides of aromatic and cycloaliphatic carboxylic acids and to methods for their preparation.

Bis-N-chloramides are valuable intermediate compounds, which, among other things, can be used for the preparation of diurethanes, di-ureas, diamines and diisocyanates. So far, only adipic, pimelic, suberic and sebacic acid-bis-N-chloramides have become known from German Pat. No. 909 455 and a publication by Eckert et al. in Rayon+Synthetics+Rayon Staple, 29, pp. 43–53 (1951) as aliphatic representatives of this class of substances. According to the processes described there, these compounds can be prepared with a yield of 37 to 95%.

On the other hand, no suitable process has been known so far for the preparation of aromatic bis-N-chloramides. Only U.S. Pat. No. 3,105,848 describes the preparation of isophthalic bis-N-chloramide by means of the chlorination of isophthalic acid amide. However, when this known process is worked, one obtains isophthalic acid-bis-N-chloramide only in a yield of 3.5% of the theory. Preparation according to this process of the isomeric terephthalic acid-bis-N-chloramide is not possible at all.

Only recently has it become possible to prepare the terephthalic acid-, as well as the isopthalic acid-bis-N-chloramide with a high yield according to a process described in Belgian Pat. No. 812 357. Cycloaliphatic and additional aromatic bis-N-chloramides have so far not become known.

Because of the importance of bis-N-chloramides as preliminary products for industrially important diisocyanates, there has existed a need to create additional compounds of this class substance.

GENERAL DESCRIPTION OF THE INVENTION

The present invention relates to new bis-N-chloramides of the formula

Cl—NH—CO—X—CO—NH—Cl wherein X is selected from the group consisting of a residue of the formula:

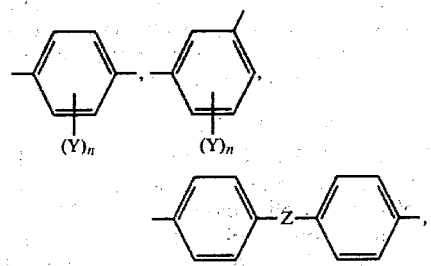

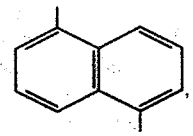

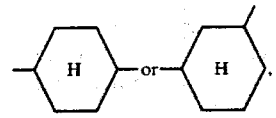

in which Y is at least one of a lower alkyl residue having 1 to 4 carbon atoms, and Z is an oxygen or sulfur atom, or an —SO$_2$— or an alkylene group with 1 to 4 carbon atoms, and n is an integer from 1 to 4.

In the above formula, wherein Y stands for 1 or several lower alkyl residues, i.e. in the case of a phenylene residue with several substituents, these may be identical or different.

Among the novel compounds according to the invention are the following bis-N-chloramides:
4-Methyl isophthalic acid bis-N-chloramide
Methyl terephthalic acid-bis-N-chloramide
Diphenyl ether-4,4'-dicarboxylic acid bis-N-chloramide
Diphenyl thioether-4,4'-dicarboxylic acid bis-N-chloramide
Diphenyl sulfone-4,4'-dicarboxylic acid bis-N-chloramide
Ethylene-1,2-bis-phenyl-4,4'-dicarboxylic acid bis-N-chloramide
Cyclohexane-1,4,-dicarboxylic acid bis-N-chloramide
Cyclohexane-1,3-dicarboxylic acid bis-N-chloramide
Napthalene-2,6-dicarboxylic and bis-N-chloramide The compounds pursuant to the invention are obtained through chlorination of the pertinent dicarboxylic acid amines. The process conditions to be used thereby vary accordingly.

Pursuant to the invention, preparation of the substituted terephthalic and isophthalic acid-bis-N-chloramides is carried out in such a way, that a benzene dicarboxylic acid amide of the general formula

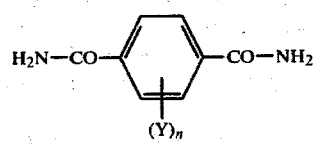

or

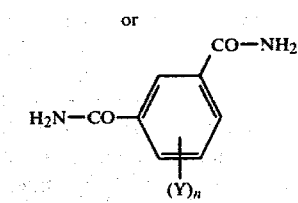

wherein X and n have the above-mentioned meaning, is chlorinated in an aqueous mineral acid at temperatures from 0° to 40° C. When use is made of this method, one obtains for example the 4-methylisophthalic acid-bis-N-chloramide and the methyl-terephthalic acid-bis-N-chloramide with excellent yield.

The cyclohexane-1,4-bis-N-chloramide, the cyclohexane-1,3-bis-N-chloramide and the diphenyl ether- 4,4‴-dicarboxylic acid-bis-N-chloramide are also advantageously prepared through chlorination of the pertinent diamides, i.e. of the cyclohexane-1,4-dicarboxylic acid amide, the cyclohexane-1,3-dicarboxylic acid amide, or the diphenyl ether-4,4′dicarboxylic acid amine, in an aqueous mineral acid at temperatures from 0° to 40° C.

Suitable mineral acids are e.g. dilute, aqueous hydrochloric acid (1% to 25%), sulfuric acid (1% to 10%), and phosphoric acid (1% to 10%). Preferably, use is initially made of a neutral, aqueous suspension of the amides, whereby the hydrogen chloride forming as by-product during chlorination dissolves in the reaction mixture and conversion thus takes place in a dilute aqueous-hydrochloric medium. Preferably, a start is furthermore made with dilute, hydrochloric or dilute sulfuric acid aqueous suspensions of the amides.

Some of the bis-N-chloramides according to the invention are not obtainable according to the above-described chlorination process in a mineral acid medium. This applies for example to ethylene-1,2-bis-phenyl-4,4′-carboxylic acid-bis-N-chloramide and to naphthalene-2,6-dicarboxylic acid-bis-N-chloramide. These compounds can for example also not be chlorinated under higher chlorine pressures or in glacial acetic acid. Pursuant to the invention they are prepared in such a way that the appropriate diamides, i.e. ethylene-1,2-bis-phenyl-4,4′-carboxylic acid amide, or naphthalene-2,6-dicarboxylic acid amide are chlorinated in a mixture of glacial acetic acid and an alkali acetate, preferably sodium acetate, at temperatures from 10° to 30° C. Chlorination of the acid amides proceeds exothermically. The process pursuant to the invention is carried out at temperatures from 0° to 40° C. The utilization of higher temperatures is disadvantageous to the extent that under these conditions, noticeable quantities of the corresponding dicarboxylic acid are formed through hydrolysis. For economic reasons, chlorination is preferably carried out at 5° to 25° C., whereby the heat of reaction can be removed by cooling with water.

The process according to the invention can be carried out at normal pressure, as well as at elevated pressures. It is true that the required reaction time becomes shorter with increasing pressure, but, for economic reasons, the preferred pressure range is between about 1 and 6 kg/cm$^2$.

Since, in the process pursuant to the invention, chlorination takes place in the heterogeneous phase, care must be taken that the suspension is properly mixed. The reaction mixture should be at least diluted to such an extent that it can be stirred, or mixed in some other way, without difficulties. The preferred dilution of the reaction batch amounts to about 100 to 200 grams of amide per liter of water, or aqueous mineral acid.

When the mentioned process conditions are maintained, chlorination is terminated after about 0.25 to 2 hours. The amide is practically quantitatively converted to the bis-N-chloramide, without any solution taking place in the interim. After terminated chlorination, the resulting suspension contains as solid substance merely the N-chloramide. The products can be separated in the most simple way, e.g. through filtration or centrifuging. After washing, e.g. with cold water, and drying at e.g. 50° C. in a vacuum, they are obtained in highest purity.

DESCRIPTION OF THE PREFERRED EMBODIMENTS

The following examples illustrate the invention, but are not to be regarded as limiting:

EXAMPLE 1

53.4 g (0.3 mol) of 4-methyl isophthalic acid diamide were suspended in 1.5 liters of 15% aqueous hydrochloric acid, cooled to 10° C., and a strong stream of chlorine passed through within a period of 4 hrs with vigorous agitation. The white reaction material was then filtered off with suction, and washed with water until neutral. 68.5 g (=92.4% of the theory) of 4-methyl isophthalic acid-bis-N-chloramide were isolated after drying.

EXAMPLE 2

Methyl terephthalic acid diamide was subjected to chlorination analogous to Example 1. 121 g (0.68 mol) of methyl terephthalic acid diamide were suspended in 2.0 liters of 15% aqueous hydrochloric acid and a moderate stream of chlorine was conducted through the suspension for 6 hrs at about 10° C., with vigorous agitation. After termination of the conversion, the formed methyl terephthalic acid-bis-N-chloramide was filtered through a frit and washed with water until neutral. 161.5 g (=96% of the theory) of the desired methyl terephthalic acid-bis-N-chloramide remained after drying.

EXAMPLE 3

9.33 of cyclohexane-1,4-dicarboxylic acid diamide (55 mmol) were chlorinated in the course of 1 hr at 5° C. in 150 ml of 15% HCl, analogous to Example 1. After suction, washing until neutral and drying over P$_2$O$_5$, there remained 11.94 g (=96% of the theory) of cyclohexane-1,4-bis-N-chloramide.

EXAMPLE 4

Analogous to Examples 1 to 3, 51.3 g (0.20 mol) of diphenylether-4,4′-dicarboxylic acid diamide were chlorinated in the course of 4 hrs at 15° to 20° C. in 2.5 liters of 5% hydrochloric acid with vigorous agitation. Further processing was carried out analogous to Examples 1 to 3. 63 g (=100% of the theory) of the diphenylether-4,4′-dicarboxylic acid-bis-N-chloramide in the form of a white powder were obtained.

EXAMPLE 5

17 g (=63.5 mmol) of ethylene-1,2-bis-phenyl-4,4′-carboxylic acid amide were suspended in a solution of 500 ml glacial acetic acid and 10.4 g (0.127 mol) sodium acetate, with vigorous agitation. After chlorination for 6 hrs, the yellow suspension was dried by suction and subsequently washed twice, each time with 30 ml of glacial acetic acid and after that twice, each time with 50 ml of water. In this way it was possible to isolate a total of 18.5 g (=86% of the theory) of ethylene-1,2-bis-phenyl-4,4′-carboxylic acid-bis-N-chloramide in the form of a colorless, fine-grained powder.

EXAMPLE 6

Analogous to Example 5, 21.4 g (0.1 mol) of 2,6-naphthalene dicarboxylic acid diamide were added to a solution of 500 ml of glacial acetic acid and 18 g (0.22 mol) sodium acetate with vigorous agitation. During 5 hrs a finely divided stream of chlorine was conducted at room temperature into the well-stirred suspension. After termination of the reaction, the white precipitate was dried by suction through a glass frit and washed three times, each time with 20 ml of cold water. 28.1 g (=99% of the theory) of naphthalene-2,6-dicarboxylic acid-bis-N-chloramide, in the form of a fine, colorless powder, remained after drying.

What is claimed is:

1. A process for the preparation of a bis-N-chloramide of cyclohexane-1,4-dicarboxylic acid, comprising chlorinating the corresponding diamide of said acid with chlorine in a medium consisting essentially of an aqueous mineral acid at a temperature between 0° and 4° C.

2. The process of claim 1 in which said diamide is initially in the form of a neutral suspension.

3. The process of claim 1 in which said diamide is in the form of a suspension in dilute hydrochloric acid.

* * * * *